United States Patent
Suri

(10) Patent No.: US 12,232,941 B2
(45) Date of Patent: Feb. 25, 2025

(54) FIRST AID KIT ALERT SYSTEM AND A VEHICLE HAVING THE SAME

(71) Applicant: GM GLOBAL TECHNOLOGY OPERATIONS LLC, Detroit, MI (US)

(72) Inventor: Venkata Suresh Dayakar Suri, Bengaluru (IN)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 134 days.

(21) Appl. No.: 18/307,339

(22) Filed: Apr. 26, 2023

(65) Prior Publication Data

US 2024/0358562 A1    Oct. 31, 2024

(51) Int. Cl.
*A61F 17/00*    (2006.01)
*B60R 21/013*    (2006.01)

(52) U.S. Cl.
CPC ............ *A61F 17/00* (2013.01); *B60R 21/013* (2013.01)

(58) Field of Classification Search
CPC .............................. A61F 17/00; B60R 21/013
See application file for complete search history.

(56) References Cited

U.S. PATENT DOCUMENTS 10,820,636 B2 *    11/2020    Hanna ..................... A41D 31/24

\* cited by examiner

*Primary Examiner* — Benyam Haile
(74) *Attorney, Agent, or Firm* — CANTOR COLBURN LLP

(57) ABSTRACT

A vehicle having a first aid kit having a plurality of content items is provided. The vehicle also includes one or more impact sensors and a controller. The controller is configured to detect, using the impact sensors, a collision involving the vehicle and activate a door of the first aid kit to expose the plurality of content items to an interior of the vehicle and activating an indicator disposed on the first aid kit based on a determination that a force of the collision exceeds a first threshold value. Based on a determination that the force of the collision exceeds a second threshold value and is less than the first threshold value, the controller is configured to activate the indicator disposed on the first aid kit.

20 Claims, 6 Drawing Sheets

FIRST AID KIT ALERT SYSTEM AND A VEHICLE HAVING THE SAME

INTRODUCTION

The disclosure relates to a first aid kit alert system. More specifically, the disclosure relates to a vehicle having a first aid kit alert system and method for operating the same.

Motor vehicles often contain first aid kits that are located in a glove box or other location in the vehicle. These first aid kits typically include medical supplies that may be used by the occupant of a vehicle to treat minor medical injuries. Since the occupant of the vehicle does not access the first aid kits frequently, the occupant may not be aware of the existence or location of the first aid kit in the vehicle. As a result, the occupants may not utilize the first aid kit when it is needed.

SUMMARY

In one exemplary embodiment, a method for management of a first aid kit disposed in a vehicle is provided. The method includes detecting a collision involving the vehicle and based on a determination that a force of the collision exceeds a first threshold value, activating a door to expose contents of the first aid kit to an interior of the vehicle and activating an indicator disposed on the first aid kit. The method also includes activating the indicator disposed on the first aid kit based on a determination that the force of the collision exceeds a second threshold value and is less than the first threshold value.

In addition to the one or more features described herein the indicator includes a light and activating the indicator includes flashing the light.

In addition to the one or more features described herein the indicator includes a speaker and activating the indicator includes playing a sound via the speaker.

In addition to the one or more features described herein the method also includes displaying an alert that the first aid kit needs service based on a determination that one or more items have been removed from the first aid kit.

In addition to the one or more features described herein the method also includes displaying an alert that the first aid kit needs service based on a determination that one or more items of the first aid kit have reached an expiration date.

In addition to the one or more features described herein the method also includes providing a voice request to occupants of the vehicle to determine whether an occupant needs the first aid kit based on a determination that the force of the collision exceeds a second threshold value and is less than the first threshold value and activating the door to expose contents of the first aid kit to the interior of the vehicle based on receiving a positive response from the occupant.

In addition to the one or more features described herein the first aid kit includes one or more medical supplies, a flashlight, an automotive glass-breaking device, and a seat-belt-cutting device.

In addition to the one or more features described herein the one or more medical supplies are determined at least in part based on a medical condition of an operator of the vehicle.

In one exemplary embodiment, a vehicle is provided. The vehicle includes a first aid kit having a plurality of content items, one or more impact sensors, and a controller. The controller is configured to detect, using the impact sensors, a collision involving the vehicle and activate a door of the first aid kit to expose the plurality of content items to an interior of the vehicle and activating an indicator disposed on the first aid kit based on a determination that a force of the collision exceeds a first threshold value. The controller is also configured to activate the indicator disposed on the first aid kit based on a determination that the force of the collision exceeds a second threshold value and is less than the first threshold value.

In addition to the one or more features described herein the indicator includes a light and activating the indicator includes flashing the light.

In addition to the one or more features described herein the indicator includes a speaker and activating the indicator includes playing a sound via the speaker.

In addition to the one or more features described herein the first aid includes a camera configured to monitor a presence of the plurality of content items.

In addition to the one or more features described herein the controller is further configured to display an alert that the first aid kit needs service based on a determination that one or more items have been removed from the first aid kit.

In addition to the one or more features described herein the controller is further configured to display an alert that the first aid kit needs service based on a determination that one or more items of the first aid kit have reached an expiration date.

In addition to the one or more features described herein the controller is further configured to provide a voice request to occupants of the vehicle to determine whether an occupant needs the first aid kit based on a determination that the force of the collision exceeds a second threshold value and is less than the first threshold value and activate the door to expose contents of the first aid kit to the interior of the vehicle based on receiving a positive response from the occupant.

In addition to the one or more features described herein the first aid kit includes one or more medical supplies, a flashlight, an automotive glass-breaking device, and a seat-belt-cutting device.

In addition to the one or more features described herein the one or more medical supplies are determined at least in part based on a medical condition of an operator of the vehicle.

In one exemplary embodiment, a vehicle is provided. The vehicle includes a first aid kit having a plurality of content items and one or more sensors configured to monitor a presence of the plurality of content items, one or more impact sensors, and a controller. The controller is configured to detect, using the impact sensors, a collision involving the vehicle and activate a door of the first aid kit to expose the plurality of content items to an interior of the vehicle and activating an indicator disposed on the first aid kit based on a determination that a force of the collision exceeds a first threshold value. The controller is also configured to activate the indicator disposed on the first aid kit based on a determination that the force of the collision exceeds a second threshold value and is less than the first threshold value.

In addition to the one or more features described herein the indicator includes a light and activating the indicator includes flashing the light.

In addition to the one or more features described herein the controller is further configured to display an alert that the first aid kit needs service based on a determination that one or more items have been removed from the first aid kit.

The above features and advantages, and other features and advantages of the disclosure are readily apparent from the following detailed description when taken in connection with the accompanying drawings.

BRIEF DESCRIPTION OF THE DRAWINGS

Other features, advantages and details appear, by way of example only, in the following detailed description, the detailed description referring to the drawings in which.

DETAILED DESCRIPTION

Figure 1:
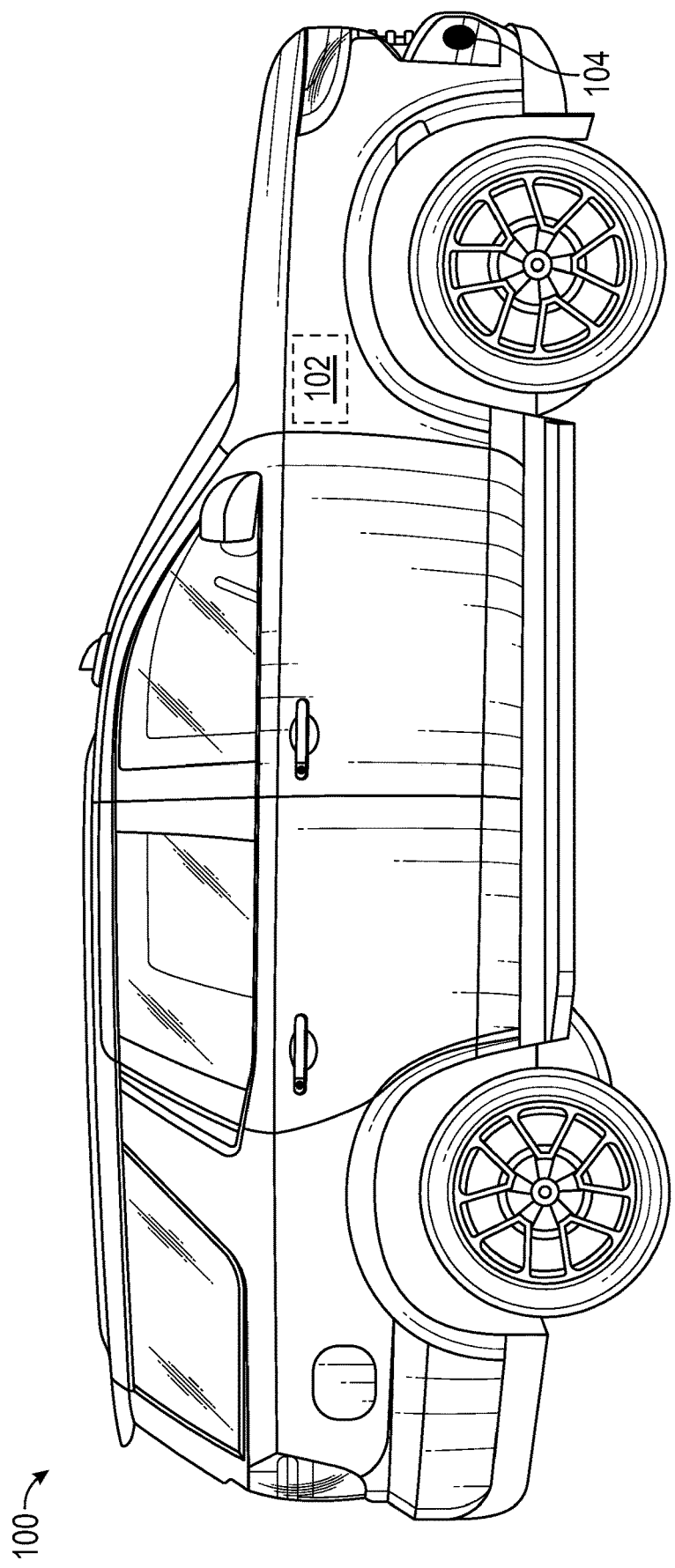
FIG. 1 is a schematic diagram of a vehicle in accordance with an exemplary embodiment.

The following description is merely exemplary in nature and is not intended to limit the present disclosure, its application, or uses. Various embodiments of the disclosure are described herein with reference to the related drawings. Alternative embodiments of the disclosure can be devised without departing from the scope of the claims. Various connections and positional relationships (e.g., over, below, adjacent, etc.) are set forth between elements in the following description and in the drawings. These connections and/or positional relationships, unless specified otherwise, can be direct or indirect, and the present disclosure is not intended to be limiting in this respect. Accordingly, a coupling of entities can refer to either a direct or an indirect coupling, and a positional relationship between entities can be a direct or indirect positional relationship.

Turning now to an overview of the aspects of the disclosure, embodiments of the disclosure include systems and methods for managing a first aid kit located in a vehicle. In exemplary embodiments, the vehicle is configured to alert an occupant to the existence and location of a first aid kit upon detecting that the vehicle was involved in a collision. In addition, the vehicle is configured to alert an occupant to the existence and location of a first aid kit upon detecting that the occupant has initiated a distress signal. In one embodiment, the nature of the alert provided to the occupant is based on a determined severity of the detected collision. In exemplary embodiments, the system for managing the first aid kit is configured to monitor the contents of the first aid kid and to cause an alert to be displayed in the vehicle that one of the content items of the first aid kit is in need of replacement.

Referring now to FIG. 1, a schematic diagram of a vehicle 100 in accordance with an exemplary embodiment is shown. In exemplary embodiments, the vehicle 100 includes a controller 102 and one or more sensors 104. In exemplary embodiments, the controller 102 is one of a general-purpose processor, a Field Programmable Gate Array (FPGA), an application-specific integrated circuit (ASIC), or the like. The controller 102 is configured to monitor the sensors 104. The sensors 104 are configured to monitor the condition of vehicle 100, detect the occurrence of an impact involving vehicle 100, and quantify the force of that impact.

Figure 2B:
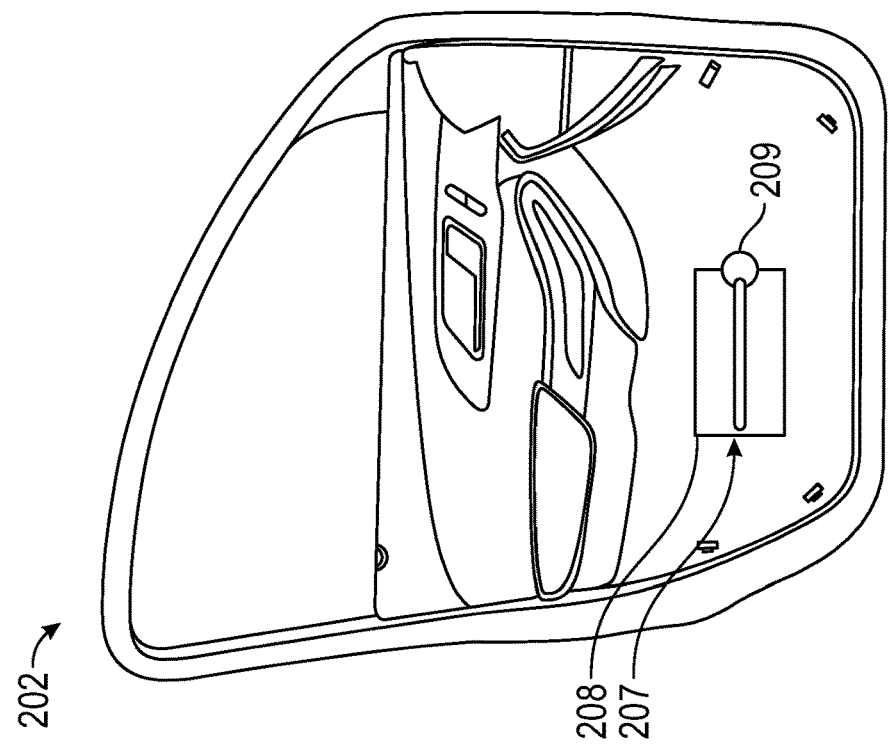
FIGS. 2A and 2B are schematic diagrams illustrating different portions of an interior of a vehicle in accordance with an exemplary embodiment.
Figure 2A:
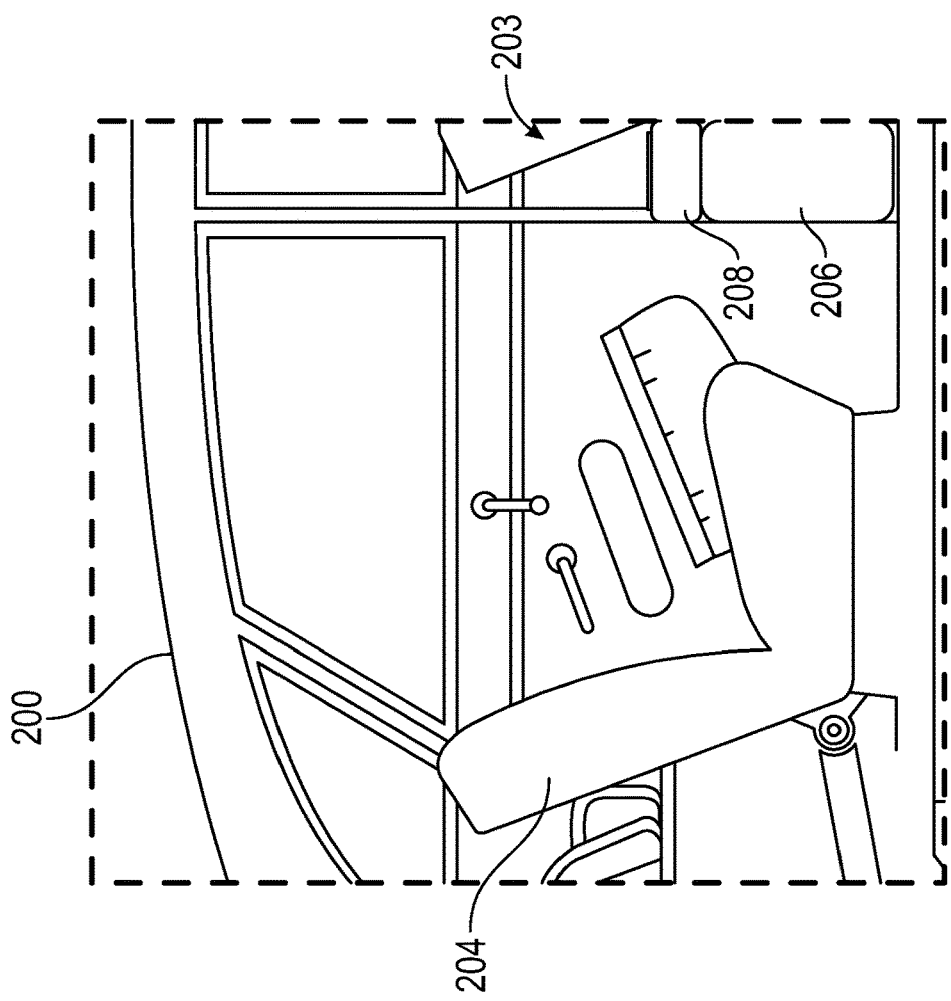

Referring now to FIGS. 2A and 2B, schematic diagrams illustrating different portions of the interior of vehicle 200 in accordance with an exemplary embodiment are shown. In one embodiment, as shown in FIG. 2A, a center console 206 is disposed between two front seats 203 and in front of a rear seat 204. The center console 206 includes a first aid kit 208 disposed inside of the center console 206. In another embodiment, as shown in FIG. 2B, door 202 of a vehicle includes a first aid kit 208 disposed on an interior surface. In one embodiment, the first aid kit 208 includes an indicator light 209 disposed on the outer surface of the first aid kit 208. The first aid kit 208 also includes a door 207 that is opened to access the contents of the first aid kit 208.

Figure 3B:
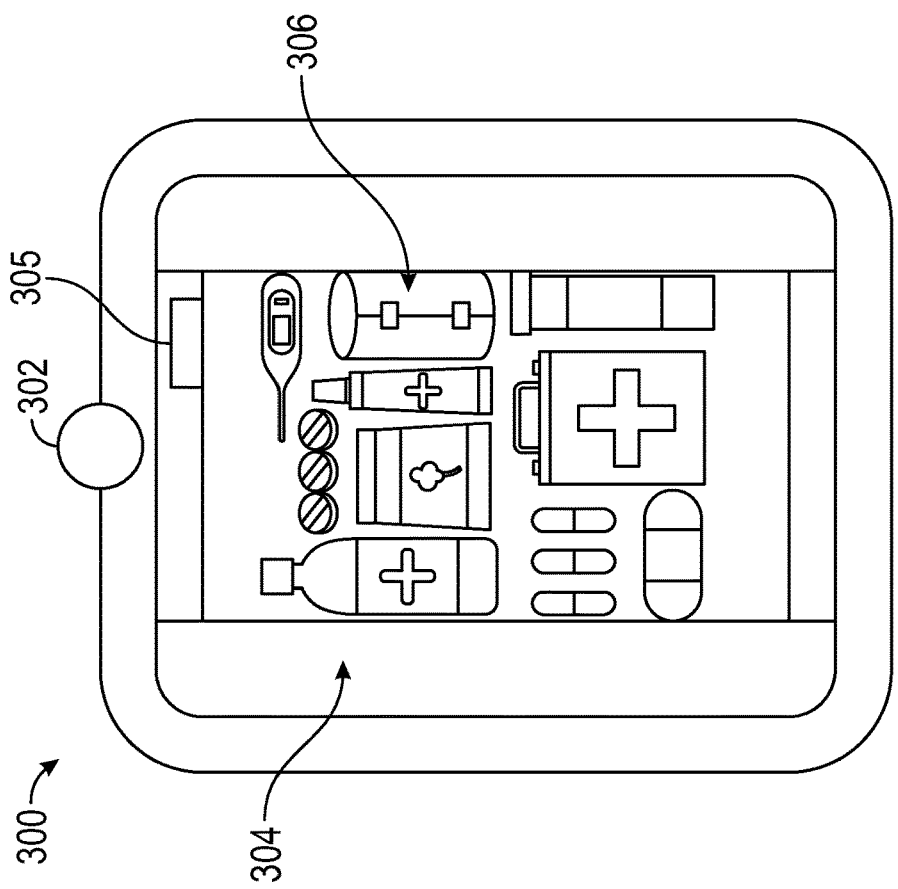
FIG. 3B is a schematic diagram illustrating a first aid kit in an open position in accordance with an exemplary embodiment.
Figure 3A:
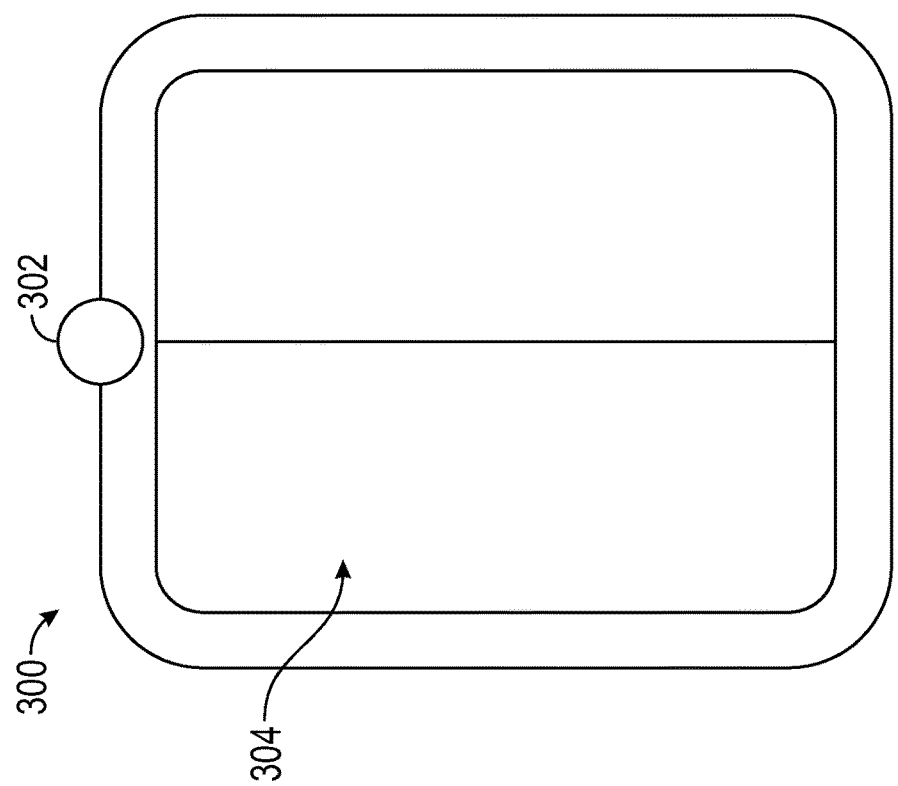
FIG. 3A is a schematic diagram illustrating a first aid kit in a closed position in accordance with an exemplary embodiment.

FIG. 3A is a schematic diagram illustrating a first aid kit 300 in a closed position in accordance with an exemplary embodiment. The first aid kit 300 includes an indicator 302 disposed on the outer surface of the first aid kit 300 that is configured to draw the attention of the occupants of the vehicle to the first aid kit 300. The first aid kit 300 also includes one or more doors 304 that are opened to access the contents of the first aid kit 300. FIG. 3B is a schematic diagram illustrating the first aid kit 300 in an open position in accordance with an exemplary embodiment. In the open position, the doors 304 have been moved to make the contents 306 of the first aid kit 300 accessible to the occupants of the vehicle.

In exemplary embodiments, the indicator 302 of the first aid kit 300 is selectively activated by a controller of the vehicle based on detecting that the vehicle has been involved in a collision. The indicator 302 may include a light such as a light-emitting diode, an incandescent, or any other suitable light source. The light of the indicator 302 may be configured to flash or strobe when activated by the controller. In some embodiments, the indicator 302 includes a speaker that is configured to emit a sound to aid in drawing the attention of the occupants of the vehicle to the first aid kit.

In exemplary embodiments, the doors 304 of the first aid kit 300 are configured to be opened and closed automatically, in response to a signal from the controller of the vehicle. In addition, the doors 304 of the first aid kit 300 may be manually opened and closed by an occupant of the vehicle. Although the first aid kit 300 is shown as having two doors 304, it will be appreciated by those of ordinary skill in the art that different configurations of the first aid kit 300 having a single door may be used.

In exemplary embodiments, the contents 306 of the first aid kit 300 may include one or more medical supplies, a flashlight, an automotive glass-breaking device, and a seatbelt-cutting device. In one embodiment, one or more medical supplies are determined at least in part based on a medical condition of an operator of the vehicle. For example, if the owner of the vehicle is a diabetic, the contents 306 may include glucose tablets or the like. In another example, if the owner suffers from allergies, the contents 306 may include an EpiPen.

In exemplary embodiments, one or more sensors 305 are disposed within the first aid kit 300 to monitor the presence of the contents 306 of the first aid kit. In one embodiment, the sensors include a camera that is configured to capture images of the inside of the first aid kit, which are then analyzed by the controller to determine whether all of the content items are present. In another embodiment, the sensors 305 include capacitive sensors that are configured to detect when a content item is removed from the first aid kit 300.

Figure 4:
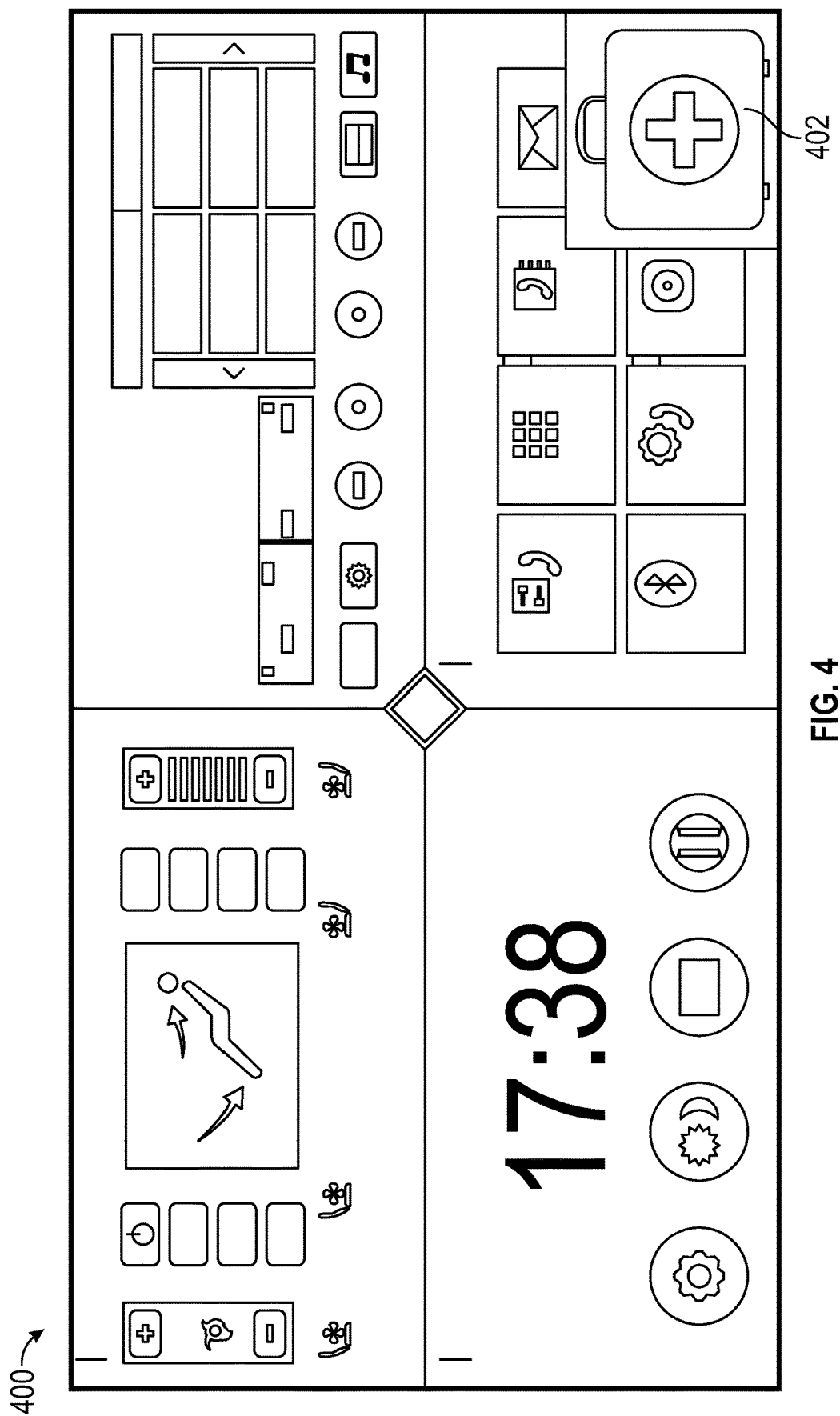
FIG. 4 is a schematic diagram illustrating a user interface of a vehicle in accordance with an exemplary embodiment.

Referring now to FIG. 4, a schematic diagram illustrating a user interface 400 of a vehicle in accordance with an exemplary embodiment is shown. In exemplary embodiments, the user interface 400 includes controls for one or more systems of the vehicle such as the air conditioning, the infotainment system, and the like. The user interface 400 is further configured to display icon 402 which provides the user with the status of the first aid kit. In exemplary embodiments, the status of the first aid kit is one of in need of service and not in need of service. In one embodiment, a controller instructs the user interface 400 to display an icon 402 that indicates that the first aid kit needs service, (e.g., a red icon) based on a determination that one or more items have been removed from the first aid kit or that one or more items of the first aid kit have reached an expiration date. Based on a determination that all of the contents are present in the first aid kit and that none of the items of the first aid kit has reached an expiration date. The controller instructs the user interface to display an icon 402 (e.g., a green icon) that indicates that the first aid kit does not need service.

Figure 5:
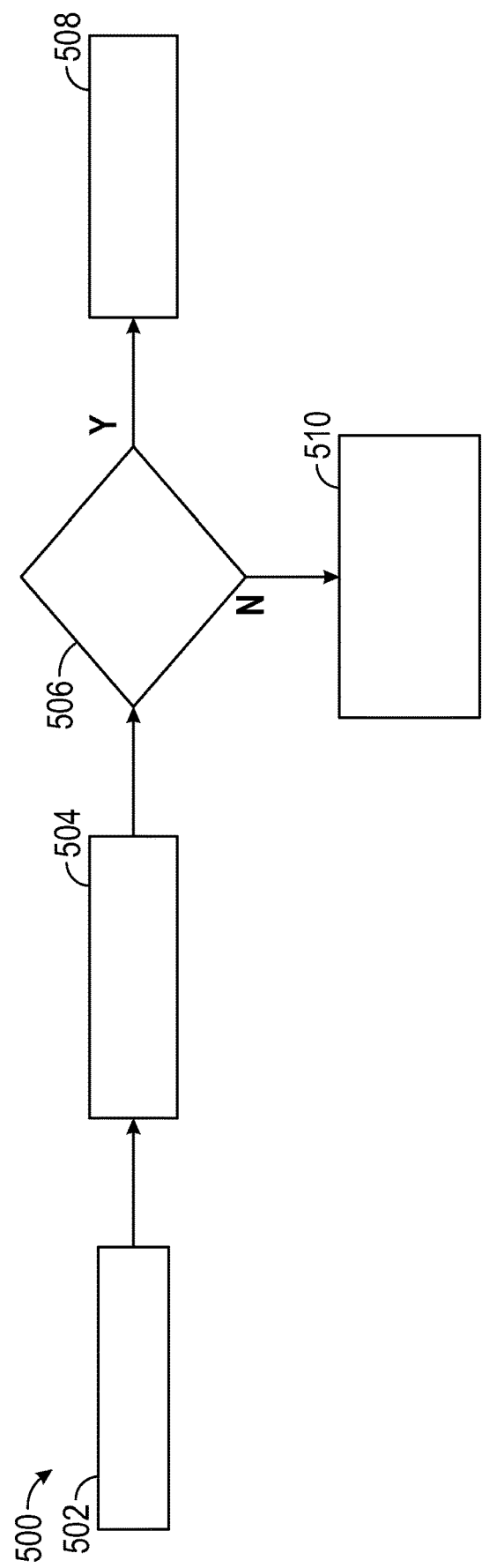
FIG. 5 is a flowchart illustrating a method for verifying the status of the first aid kit of a vehicle in accordance with an exemplary embodiment.

Referring now to FIG. 5, a flowchart illustrating a method 500 for verifying the status of the first aid kit of a vehicle in accordance with an exemplary embodiment is shown. In exemplary embodiments, the method 500 is performed by a controller of a vehicle, such as the one shown in FIG. 1. The method 500 begins a block 502 when a vehicle is started. Next, at block 504, the method 500 includes checking the first aid kit to determine whether all of the contents of the first aid kit are present and that none of the items of the first aid kit have reached their expiration date. Based on a determination at block 506 that one of the items of the first aid kit has reached its expiration date or that one of the items is missing from the first aid kit, the method 500 proceeds to block 510 and displays an icon on the user interface that indicates that the first aid kit needs service. Otherwise, based on a determination that all of the contents of the first aid kit are present and that none of the items of the first aid kit have reached their expiration date, the method 500 proceeds to block 508 and displays an icon on the user interface that indicates that the first aid kit does not need of service. In alternative embodiments, only an icon indicating that the first aid kit needs service is provided via the user interface.

Figure 6:
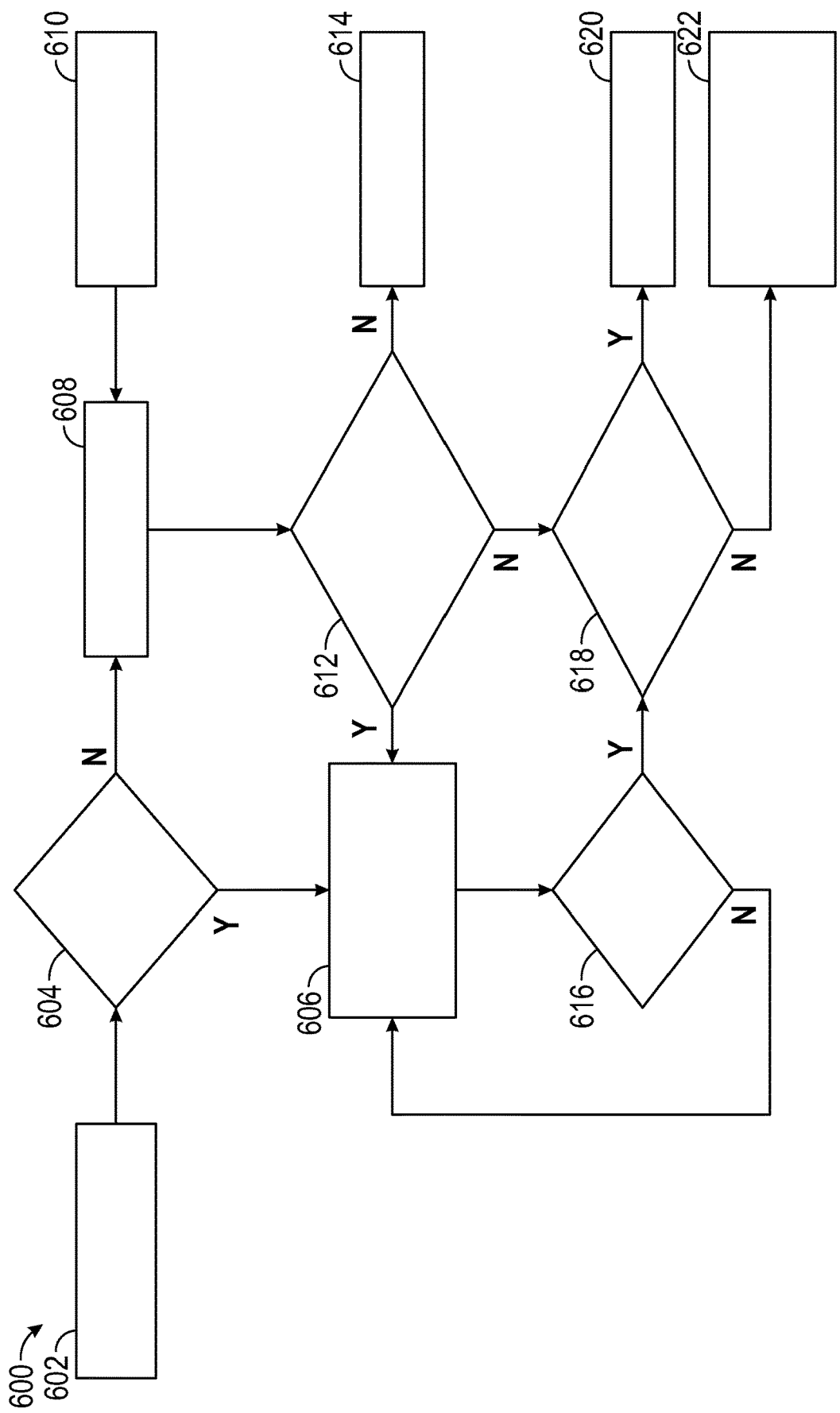
FIG. 6 is a flowchart illustrating a method for operating a first aid alert system of a vehicle in accordance with an exemplary embodiment.

Referring now to FIG. 6, a flowchart illustrating a method for operating a first aid alert system of a vehicle in accordance with an exemplary embodiment is shown. In exemplary embodiments, the method 600 is performed by a controller of a vehicle, such as the one shown in FIG. 1. At block 602 the method 600 includes detecting an impact to the vehicle (i.e., that the vehicle has been in a collision). Next, at decision block 604 the method 600 determines whether the force of the impact exceeds a first threshold value. In one embodiment, the first threshold value is a level of force that is sufficient to cause the deployment of one or more airbags in the vehicle. Based on a determination that the force of the impact exceeds the first threshold value, the method 600 proceeds to block 606.

Based on a determination that the force of the impact does not exceed the first threshold value, the method 600 proceeds to block 608 and an indicator disposed on the first aid kit is activated. In exemplary embodiments, the indicator may include a flashing light and/or a sound emitted from a speaker. At block 610, the method 600 includes detecting that an occupant of the vehicle has initiated a distress signal. In exemplary embodiments, the distress signal is initiated by an occupant pressing an S.O.S. button or icon on the user interface disposed in the vehicle.

Next, at decision block 612, the method 600 includes providing a request to the occupants of the vehicle to determine whether the occupants are in need of the first aid kit. Based on receiving a positive response from the occupants, the method 600 proceeds to block 606. Based on receiving a negative response from the occupants, the method 600 proceeds to block 618. Based on receiving no response from the occupants, the method 600 proceeds to block 618. In one embodiment, the request to, and response from, the occupants of the vehicle are voice requests. In another embodiment, the request to, and response from, the occupants of the vehicle are made via the user interface shown in FIG. 4.

At block 606, the method 600 includes opening a door of the first aid kit, activating an indicator disposed on the first aid kit, and activating a distress call from the vehicle. In exemplary embodiments, the indicator is configured to draw the attention of the occupants of the vehicle to the first aid kit. At block 614, the method 600 includes activating a distress call from the vehicle. In exemplary embodiments, the distress call is a call to 911 or another emergency response system.

Next, at decision block 616, the method 600 includes determining whether a door of the first aid kit has been returned to a closed position. Based on determining that the door of the first aid kit has been returned to the closed position, the method 600 proceeds to decision block 618 and determines whether all of the contents of the first aid kit are present and whether any of the items of the first aid kit have reached their expiration date. Based on a determination that one of the items of the first aid kit has reached its expiration date or that one of the items is missing from the first aid kit, the method 600 proceeds to block 622 and displays an icon on the user interface that indicates that the first aid kit needs service. Otherwise, based on a determination that all of the contents of the first aid kit are present and that none of the items of the first aid kit have reached their expiration date, the method 600 proceeds to block 620 and displays an icon on the user interface that indicates that the first aid kit does not need of service.

The terms "a" and "an" do not denote a limitation of quantity, but rather denote the presence of at least one of the referenced item. The term "or" means "and/or" unless clearly indicated otherwise by context. Reference throughout the specification to "an aspect", means that a particular element (e.g., feature, structure, step, or characteristic) described in connection with the aspect is included in at least one aspect described herein, and may or may not be present in other aspects. In addition, it is to be understood that the described elements may be combined in any suitable manner in the various aspects.

When an element such as a layer, film, region, or substrate is referred to as being "on" another element, it can be directly on the other element or intervening elements may also be present. In contrast, when an element is referred to as being "directly on" another element, there are no intervening elements present.

Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this disclosure belongs.

While the above disclosure has been described with reference to exemplary embodiments, it will be understood by those skilled in the art that various changes may be made and equivalents may be substituted for elements thereof without departing from its scope. In addition, many modifications may be made to adapt a particular situation or material to the teachings of the disclosure without departing from the essential scope thereof. Therefore, it is intended that the present disclosure not be limited to the particular embodiments disclosed, but will include all embodiments falling within the scope thereof.

What is claimed is:

1. A method for management of a first aid kit disposed in a vehicle, the method comprising:
   detecting a collision involving the vehicle;
   based on a determination that a force of the collision exceeds a first threshold value, activating a door to expose contents of the first aid kit to an interior of the vehicle and activating an indicator disposed on the first aid kit; and
   based on a determination that the force of the collision exceeds a second threshold value and is less than the first threshold value, activating the indicator disposed on the first aid kit.

2. The method of claim 1, wherein the indicator includes a light and activating the indicator includes flashing the light.

3. The method of claim 1, wherein the indicator includes a speaker and activating the indicator includes playing a sound via the speaker.

4. The method of claim 1, further comprising displaying an alert that the first aid kit needs service based on a determination that one or more items have been removed from the first aid kit.

5. The method of claim 1, further comprising displaying an alert that the first aid kit needs service based on a determination that one or more items of the first aid kit have reached an expiration date.

6. The method of claim 1, further comprising:
   providing a voice request to occupants of the vehicle to determine whether an occupant needs the first aid kit based on a determination that the force of the collision exceeds a second threshold value and is less than the first threshold value; and
   activating the door to expose contents of the first aid kit to the interior of the vehicle based on receiving a positive response from the occupant.

7. The method of claim 1, wherein the first aid kit includes one or more medical supplies, a flashlight, an automotive glass-breaking device, and a seatbelt-cutting device.

8. The method of claim 7, wherein the one or more medical supplies are determined at least in part based on a medical condition of an operator of the vehicle.

9. A vehicle comprising:
   a first aid kit having a plurality of content items;
   one or more impact sensors; and
   a controller configured to:
      detect, using the impact sensors, a collision involving the vehicle;
      based on a determination that a force of the collision exceeds a first threshold value, activate a door of the first aid kit to expose the plurality of content items to an interior of the vehicle and activating an indicator disposed on the first aid kit; and
      based on a determination that the force of the collision exceeds a second threshold value and is less than the first threshold value, activate the indicator disposed on the first aid kit.

10. The vehicle of claim 9, wherein the indicator includes a light and activating the indicator includes flashing the light.

11. The vehicle of claim 9, wherein the indicator includes a speaker and activating the indicator includes playing a sound via the speaker.

12. The vehicle of claim 9, wherein the first aid kit includes a camera configured to monitor a presence of the plurality of content items.

13. The vehicle of claim 12, wherein the controller is further configured to display an alert that the first aid kit needs service based on a determination that one or more items have been removed from the first aid kit.

14. The vehicle of claim 9, wherein the controller is further configured to display an alert that the first aid kit needs service based on a determination that one or more items of the first aid kit have reached an expiration date.

15. The vehicle of claim 9, wherein the controller is further configured to:
   provide a voice request to occupants of the vehicle to determine whether an occupant needs the first aid kit based on a determination that the force of the collision exceeds a second threshold value and is less than the first threshold value; and
   activate the door to expose contents of the first aid kit to the interior of the vehicle based on receiving a positive response from the occupant.

16. The vehicle of claim 9, wherein the first aid kit includes one or more medical supplies, a flashlight, an automotive glass-breaking device, and a seatbelt-cutting device.

17. The vehicle of claim 16, wherein the one or more medical supplies are determined at least in part based on a medical condition of an operator of the vehicle.

18. A vehicle comprising:
   a first aid kit having a plurality of content items and one or more sensors configured to monitor a presence of the plurality of content items;
   one or more impact sensors; and
   a controller configured to:
      detect, using the impact sensors, a collision involving the vehicle;
      based on a determination that a force of the collision exceeds a first threshold value, activate a door of the first aid kit to expose the plurality of content items to an interior of the vehicle and activating an indicator disposed on the first aid kit; and
      based on a determination that the force of the collision exceeds a second threshold value and is less than the first threshold value, activate the indicator disposed on the first aid kit.

19. The vehicle of claim 18, wherein the indicator includes a light and activating the indicator includes flashing the light.

20. The vehicle of claim 18, wherein the controller is further configured to display an alert that the first aid kit needs service based on a determination that one or more items have been removed from the first aid kit.

* * * * *